United States Patent
Weadock et al.

(10) Patent No.: US 9,238,123 B2
(45) Date of Patent: Jan. 19, 2016

(54) ANTIMICROBIAL DRESSING PROVIDING PERCUTANEOUS DEVICE SECUREMENT AND COVER

(75) Inventors: Kevin Weadock, Hillsborough, NJ (US); Leo B. Kriksunov, Ithaca, NY (US)

(73) Assignee: Ethicon, Inc., Somerville, NJ (US)

( * ) Notice: Subject to any disclaimer, the term of this patent is extended or adjusted under 35 U.S.C. 154(b) by 388 days.

(21) Appl. No.: 12/952,628

(22) Filed: Nov. 23, 2010

(65) Prior Publication Data

US 2012/0130315 A1 May 24, 2012

(51) Int. Cl.
*A61M 25/02* (2006.01)
*A61M 25/00* (2006.01)

(52) U.S. Cl.
CPC ....... *A61M 25/02* (2013.01); *A61M 2025/0056* (2013.01); *A61M 2025/028* (2013.01); *A61M 2025/0253* (2013.01); *A61M 2025/0273* (2013.01)

(58) Field of Classification Search
CPC ............. A61M 25/02; A61M 2025/0266; A61M 2025/0246; A61M 2025/0273; A61M 2025/0233; A61M 2039/0261; A61M 2025/0056; A61M 2025/0263; A61M 2025/028
USPC ........................ 604/174, 171, 177, 179, 180
See application file for complete search history.

(56) References Cited

U.S. PATENT DOCUMENTS

| | | | |
|---|---|---|---|
| 3,918,446 A | | 11/1975 | Buttaravoli |
| 4,579,120 A | * | 4/1986 | MacGregor ................... 600/392 |
| 4,645,492 A | * | 2/1987 | Weeks ................... A61M 25/02 |
| | | | 128/DIG. 26 |
| 4,915,694 A | | 4/1990 | Yamamoto et al. |
| D350,201 S | * | 8/1994 | Hirsch et al. ................. D24/128 |
| 5,372,589 A | | 12/1994 | Davis |
| 5,554,106 A | | 9/1996 | Layman-Spillar et al. |
| 5,620,419 A | | 4/1997 | Lui et al. |
| 5,833,665 A | * | 11/1998 | Bootman et al. ............... 604/180 |
| 5,968,000 A | | 10/1999 | Harrison et al. |
| 6,695,515 B1 | * | 2/2004 | Fleury ........................... 401/132 |
| 6,765,122 B1 | | 7/2004 | Stout |
| 7,137,968 B1 | * | 11/2006 | Burrell et al. ................. 604/180 |
| 7,723,559 B2 | | 5/2010 | Linnane et al. |
| 7,985,205 B2 | * | 7/2011 | Adams .......................... 604/174 |

\* cited by examiner

*Primary Examiner* — Emily Schmidt
*Assistant Examiner* — Lauren M Peng
(74) *Attorney, Agent, or Firm* — David R. Crichton; Leo B. Kriksunov

(57) ABSTRACT

The present invention is related to a polymeric vehicle for delivery of bioactive agents, and preferably, for the delivery of one or more bioactive agents. The invention is also directed to a percutaneous device securing and drug delivery device comprising, as a component thereof, a material which delivers antimicrobial and/or other wound-healing factors at the site of the insertion of the catheter into the body. The device, when applied as described herein, provides complete antimicrobial coverage around the entry point of a percutaneous device and, preferably for a length greater than the diameter of the device. The present invention is also directed to methods for using such devices in combination with percutaneous devices primarily to reduce site infections.

19 Claims, 16 Drawing Sheets

ANTIMICROBIAL DRESSING PROVIDING PERCUTANEOUS DEVICE SECUREMENT AND COVER

FIELD OF THE INVENTION

The present invention is related to a polymeric delivery vehicle for delivery of bioactive agents, and preferably, for the delivery of one or more bioactive agents. The invention is also directed to a percutaneous device securing and drug delivery device comprising, as a component thereof, a material which delivers antimicrobial and/or other wound-healing factors at the site of the insertion of the catheter into the body. The device, when applied as described herein, provides complete (360 degree) anti-microbial coverage around the entry point of a percutaneous device and, preferably for a length greater than the diameter of the device.

BACKGROUND OF THE INVENTION

Hospitals employ multiple strategies to prevent and/or reduce infections associated with the use percutaneous medical devices, such as antiseptic preparation of insertion sites, including the initial application of topical anti-microbial solutions such as alcohol or iodine to the insertion sites is known. A further topical ointment after insertion of the device, such as an ointment containing neomycin, polymyxin and bactracin, has been shown to prevent catheter colonization/infection.

There have also been attempts to attach a cuff to the catheters, with an anti-microbial agent impregnated in the cuff. A commercially available product sold under the trade mark BIOPATCH® is applied around percutaneous devices to prevent localized infection at the insertion site. This product is a foam material that contains an antimicrobial agent chlorhexidine gluconate. Efforts to coat the catheters with anti-microbial agents are known.

Recent efforts to use a transparent film dressing to allow a visual check on the insertion site is known see for instance U.S. Pat. No. 5,372,589, issued Dec. 13, 1994 to Davis.

In addition to infection control, there is a need for percutaneous devices to remain securely in place. Securement device are known, such as U.S. Pat. No. 3,918,446, issued Nov. 11, 1975 to Buttaravoli. The device has an upper and a lower pad, between which the intravenous device is fixed. Since the function of the device is to secure the device to the body, there is a teaching to provide an adhesive material to the bottom of lower pad, and to the bottom of the top pad. There is a mention of providing the adhesive with an antibacterial agent. The device of this patent teaches including a slit in the bottom pad of the dressing, which lies below the intravenous needle or catheter when the device is in place, allowing the intravenous device to remain in contact with the skin, and therefore limiting the infection control of the device.

U.S. Pat. No. 5,833,665 issued to Matthew Bootman et al. is directed to a wound dressing for percutaneous catheters that is comprised of a crosslinked polymer containing a bioactive agent. It discloses a radial slit that is made in the device so that it can be deployed over an already placed catheter. It also discloses and claims the use of adhesives for securing the device.

Tegaderm™-CHG is a commercial device designed to reduce the incidence of CRBSI, with the CHG being the anti-microbial agent. The CHG is intended to elute from a pad that is transparent and covered with an adhesive bandage layer. The device fails to provide 360 degree coverage around the insertion site, and thereby cannot optimally reduce the potential for CRBSI. The CHG eluting portion of the device is not placed underneath the catheter which may further limit its effectiveness. A number of other patents are teaching various single slit embodiments, including U.S. Pat. No. 7,137,968; U.S. Pat. No. 5,554,106; U.S. Pat. No. 6,765,122; U.S. Pat. No. 7,723,559; U.S. Pat. No. 4,915,694; U.S. Pat. No. 5,968,000; and U.S. Pat. No. 5,620,419.

It is an object of the present invention to provide a catheter-securing and drug delivery device which is easily applied and is made of a polymer which serves as a delivery vehicle for controlled release of a bioactive agent entirely around a percutaneous wound site.

These and other objects of the invention will be apparent from the following description and appended claims, and from practice of the invention.

SUMMARY OF THE INVENTION

The present invention is directed to a percutaneous device dressing for use with a percutaneous medical device that has punctured the skin of a patient and which has a portion of the percutaneous medical device protruding from the skin. One type of such a percutaneous device is a catheter, such as a temporary installed catheter or longer term in-dwelling catheter. The dressing of the present invention is formed of a flexible material and has upper and lower surfaces. The lower surface is the skin facing surface when in use. An optional adhesive layer is disposed on the lower surface of the dressing. The dressing also has a bioactive agent that is incorporated into the flexible material of the dressing and/or onto the surfaces of the dressing. The dressing has a channel within its lower, skin-facing surface that is adapted to surround at least a portion of the percutaneous medical device protruding from the skin. The channel can be formed by any known manufacturing techniques, for example it can be machined into the dressing, cut within the dressing, or molded during the forming of the dressing. The dressing has a shape that substantially completes a perimeter proximate to the percutaneous medical device. The dressing can independently comprise gelatin, collagen, and polysaccharides or combination thereof. The dressing can be made of a hydrogel material or a composite material at least one component of which is a hydrogel. The bioactive agent can be an antimicrobial agent, such as a chlorhexidine compound, for instance chlorhexidine gluconate or chlorhexidine acetate; silver compounds, for instance silver iodide, silver bromide, silver chloride; nano-particulate metallic silver; benzalkonium chloride; polyhexamethylene biguanide (PHMB); triclosan; antibiotics such as metronidazole; alcohol; iodine; or other known antimicrobial compounds and combinations thereof, compatible with skin and useful against a range of microorganisms for example against known skin flora such as for instance *S. aureus* and MRSA.

The present invention also relates to a method of dressing the puncture site of a percutaneous medical device for a patient using a percutaneous device dressing formed from a flexible material and having upper and lower surfaces, with the lower surface being skin facing in use. The dressing also has a bioactive agent that is incorporated into the dressing and/or onto the lower surfaces of the dressing, wherein the dressing is secured to the surface of skin and optionally to the percutaneous medical device with the help of an optional adhesive layer disposed on the lower surface of the dressing or with a help of an adhesive overdressing layer preferably in a form of adhesive thin film or adhesive bandaging tape.

The dressing further has a channel within its lower, skin-facing surface that is adapted to surround at least a portion of the percutaneous medical device protruding from the skin. In use, the dressing is applied by positioning the dressing over the percutaneous medical device with the lower surface facing the skin and the percutaneous medical device, so that the channel within the lower surface of the dressing can accept a portion of the percutaneous medical device, and to enable the dressing to surround a portion of a perimeter proximate to the percutaneous medical device at the puncture site. The lower surface of the dressing is thereby in contact with the skin surrounding the puncture site while the channel cut within the lower surface of the dressing is simultaneously in contact with a portion of the medical device protruding from the skin. Advantageously, the dressing enables nurses and physicians to position the dressing over a previously installed or secured percutaneous medical device, such as a catheter. The dressing further provides 360 degree anti-microbial coverage around catheter shaft and for a length greater than the diameter of the catheter shaft. In one embodiment the dressing is elastically resilient, and it can be attached to the catheter without using an adhesive or additional dressing.

DETAILED DESCRIPTION OF THE INVENTION

In a preferred embodiment of the present invention, the dressing is made of a polymeric carrier and a bioactive agent, wherein the bioactive agent is releasable from the polymeric carrier in a controlled manner to a wound or to the skin.

The percutaneous device dressing further optionally comprises an adhesive, generally disposed on the lower surface of the dressing and optionally within the channel for affixing the dressing to the skin and for affixing the dressing to the percutaneous medical device.

In another preferred embodiment the polymeric delivery vehicle is in the form of an elastomeric pad with a channel that is used as a wound dressing. The pad may be secured upon a wound by an adhesive water-vapor film over the pad which adheres to the skin area surrounding the wound.

The percutaneous device dressing of this invention has the advantage of ease of placement without loss of complete perimeter coverage.

Figure 1A:
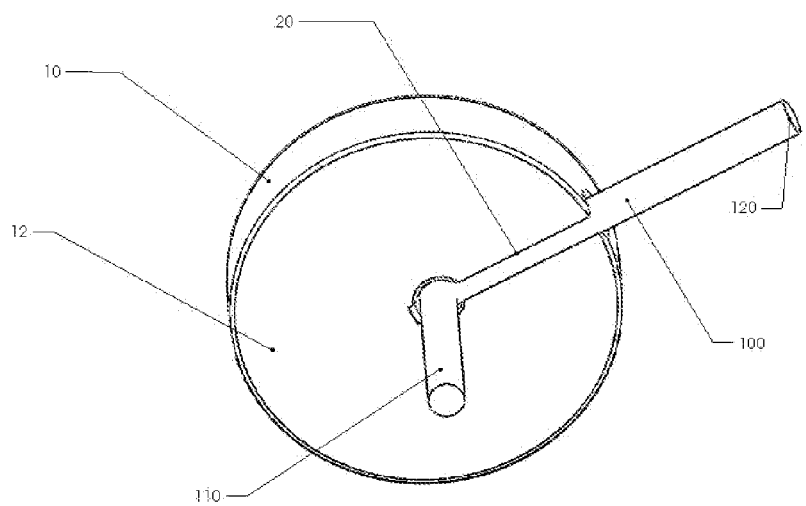
FIGS. 1a and 1b illustrate an embodiment of the inventive percutaneous medical device dressing in combination with a medical device that punctures the skin of a patient.
Figure 1B:
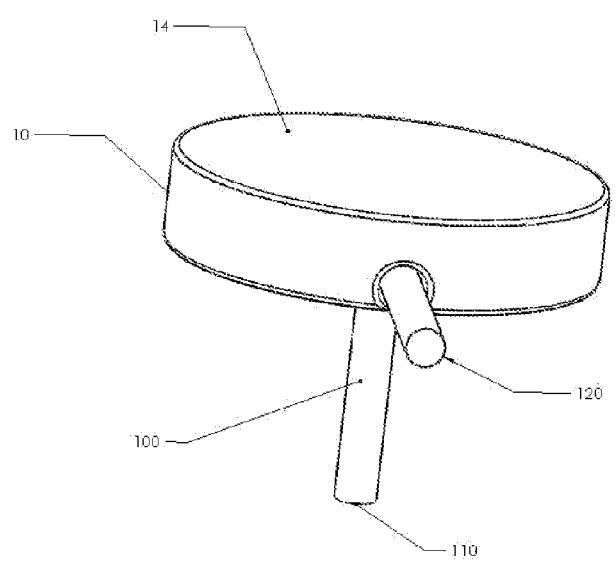

FIGS. 1a and 1b show two views of the body of dressing 10 in a shape of a pad, the body of dressing 10 having an upper surface 14 and a skin-facing lower surface 12 and further having a channel 20 cut within the body of dressing pad 10 proximal to the lower surface 12. Also shown is the percutaneous medical device 100, in the form of a catheter having a proximal end 110 piercing the skin (not shown) and disposed substantially within the patient's body (not shown) and a distal end 120 disposed substantially on the surface of skin (not shown). Channel 20 has a portion substantially parallel to the lower surface 12 and a portion substantially perpendicular to the lower surface 12 so as to accommodate within channel 20 the percutaneous medical device 100. The percutaneous medical device 100 is partially enclosed within channel 20 with the area of skin penetration around the proximal end 110 completely covered by the dressing 10 from all sides, to provide complete coverage, maintain coverage over 360 degrees around a central point over percutaneous medical device 100.

While the positioning of percutaneous medical device 100 in FIGS. 1a and 1b indicates that proximal end 110 piercing the skin is positioned under angle approximately perpendicular to the skin, the angle of percutaneous medical device 100 relative skin will vary depending on type of percutaneous medical device 100 and type of installation, from almost parallel to the skin at the point of entering the skin, to about 90 degrees or perpendicular to the skin. Typical angles can be from about 15 degrees to about 90 degrees as between percutaneous medical device 100 and the skin, such as 15, 30, 60, 80 degree angles.

Referring now to FIGS. 1 through 7, the dimensions of the channel 20 should preferably substantially conform to the size and shape of the percutaneous device 100. The dimensions of channel 20 generally conform to the dimensions of percutaneous medical device 100 so that there is a loose fit, a snug fit or a snap fit. In certain embodiments the diameter of channel 20 is about 0.95, 1.0, 1.1, or 1.2 times the size of the diameters of the outer surface of percutaneous device 100.

Figure 2A:
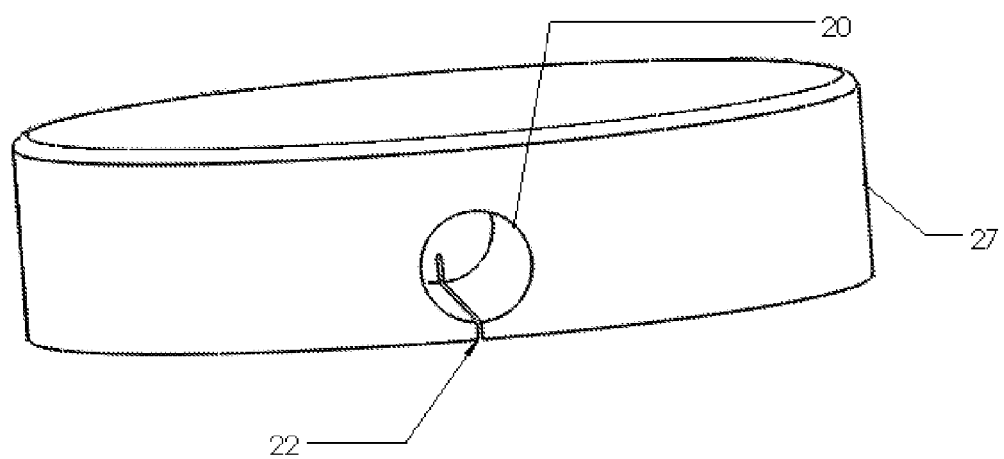
FIGS. 2a and 2b illustrate an embodiment of the inventive percutaneous medical device dressing.
Figure 2B:
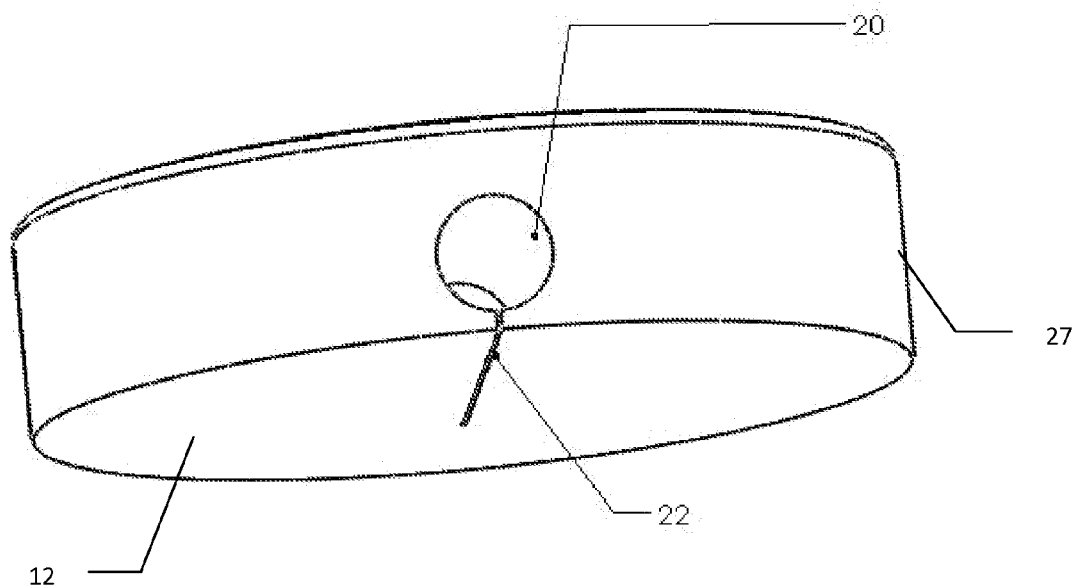
Figure 3:
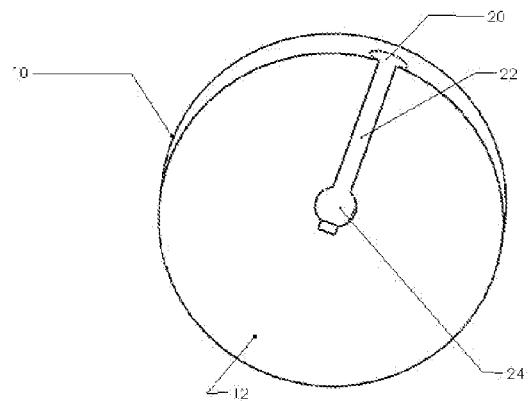
FIG. 3 illustrates an embodiment of the inventive percutaneous medical device dressing.
Figure 4:
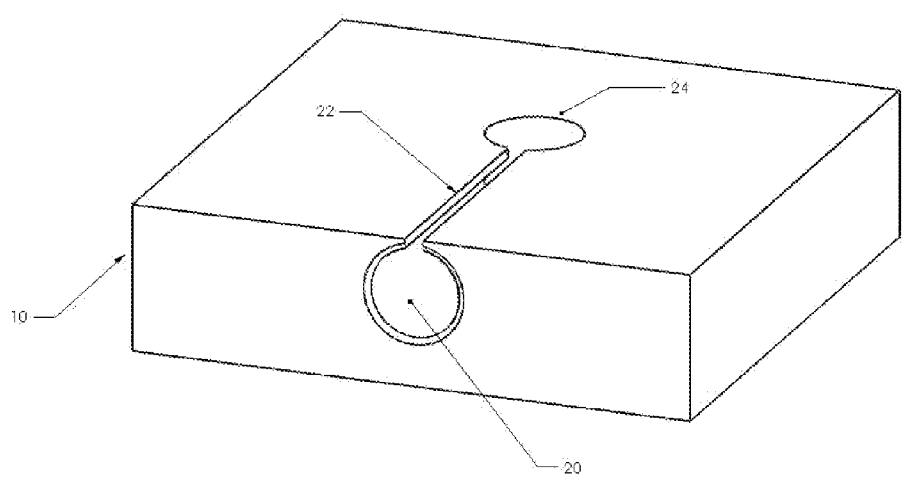
FIG. 4 illustrates an embodiment of the inventive percutaneous medical device dressing.
Figure 5:
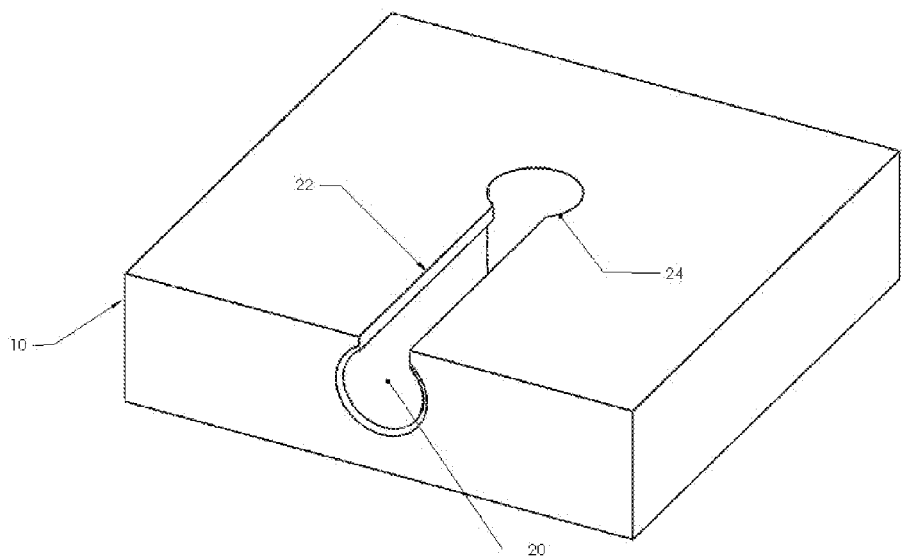
FIG. 5 illustrates an embodiment of the inventive percutaneous medical device dressing.
Figure 6:
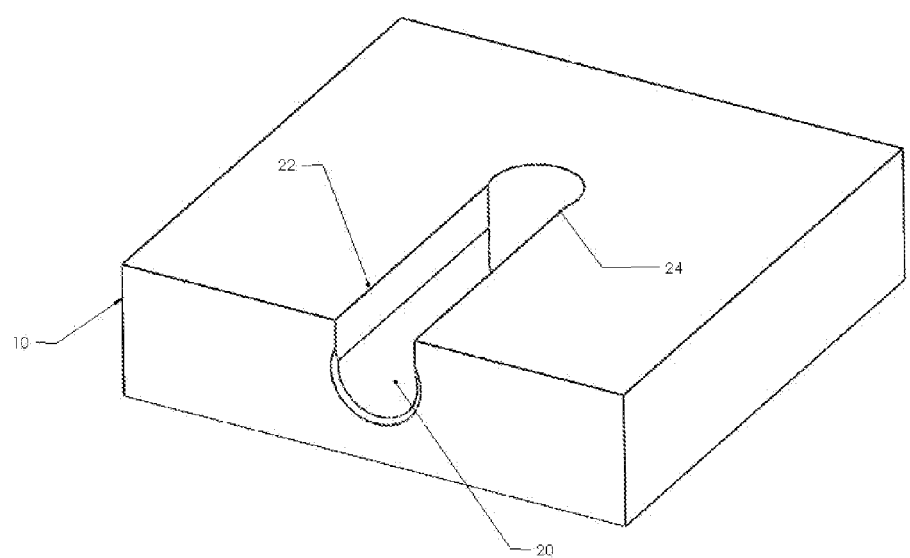
FIG. 6 illustrates an embodiment of the inventive percutaneous medical device dressing.

Gap 22 represents an opening of the channel 20 on the lower skin-facing surface 12. As illustrated in FIGS. 2a and 2b, in one embodiment gap 22 is a narrow slit with the width from about 0.01 mm to about 1 mm, such as 0.1 mm or 0.25 mm. Gap 22 can be positioned symmetrically in the center of channel 20 as shown or can be offset from the center of channel 20. As illustrated in FIGS. 1a, 1b, 3, 4, and 5, gap 22 can vary from a narrow slit to a width just under the diameter of the percutaneous medical device 100. In an illustrative example, gap 22 can vary from about 0.5 mm to about 3.5 mm for percutaneous medical device 100 having an external diameter of 4 mm and channel 20 having diameter of about 3.8 mm, 4.0 mm, or 4.2 mm. As illustrated in FIG. 6, gap 22 can also have a width that is approximately equivalent to or slightly greater than the diameter of the outer surface of percutaneous medical device 100 and diameter of channel 20.

Referring now to FIGS. 3 through 6, an optional circular opening 24 within lower surface 12 is provided to accommodate percutaneous medical device 100. Optional circular opening 24 is in communication with channel 20. Embodiments of the present invention without the optional circular opening 24 are shown in FIGS. 2a and 2b, with side wall of the dressing body shown by numeral 27. The diameter of circular opening 24 is adapted so as to accommodate percutaneous medical device 100 and can be smaller than, equivalent to, or slightly larger than the diameter of percutaneous medical device 100. In certain embodiments diameter of circular opening 24 is equivalent to about 0.8, 1.0, or 1.1 diameters of percutaneous medical device 100.

Dressing 10 is shown in FIGS. 1-7 as having generally circular or partially circular shape of the channel 20 that corresponds to a generally circular shape needed to surround a conventional percutaneous medical device. Other shapes of the channel, including elliptical and polygonal shapes, are contemplated provided that the channel 20 can accommodate the percutaneous medical device 100.

Figure 7:
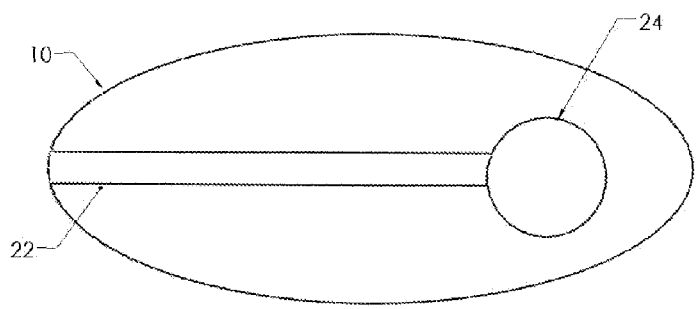
FIG. 7 illustrates an embodiment of the inventive percutaneous medical device dressing.

The outer perimeter of dressing 10 can be substantially circular as shown in FIGS. 1a, 1b, 2a, 2b, and 3, or can be different so that when in position, the exterior perimeter is elliptical, square, rectangular or irregularly shaped. Embodiments of square or rectangular shaped dressing 10 are shown in FIGS. 4, 5, and 6. Elliptical external shape of dressing 10 is illustrated by FIG. 7 showing the skin side view of dressing 10 with gap 22 and optional circular opening 24. Advantageously, the elliptical shape with offset center provides for a longer supporting path for percutaneous medical device 100 and longer path of protection against the ingress of potentially infectious matter along channel 20.

In one embodiment, dressing 10 is made of a transparent polymer or transparent or semi-transparent hydrogel thus facilitating positioning of dressing 10 over percutaneous medical device 100. In one embodiment, only the central portion of the dressing immediately surrounding the skin penetration area is transparent, such as central part of the dressing 10.

Dressing 10 is sized to cover a significant portion of catheter or percutaneous medical device 100 that protrudes from the skin, and not just the immediate skin area surrounding the penetration site. In one embodiment, the diameter of circular-shaped dressing 10 or the length of the side of the square-shaped dressing 10 is equal to from about 2 diameters of the outer surface of percutaneous medical device 100 to about 20 times the diameters of the outer surface of percutaneous medical device 100. In some embodiments the diameter of dressing 10 is equal to about 2, 3, 4, or 5 times the diameters of the outer surface of percutaneous medical device 100.

Dressing 10 is applied around catheter or percutaneous medical device 100 with lower surface 12 of dressing 10 facing the percutaneous medical device 100 such that the percutaneous medical device 100 enters channel 20 through gap 22.

Figure 8:
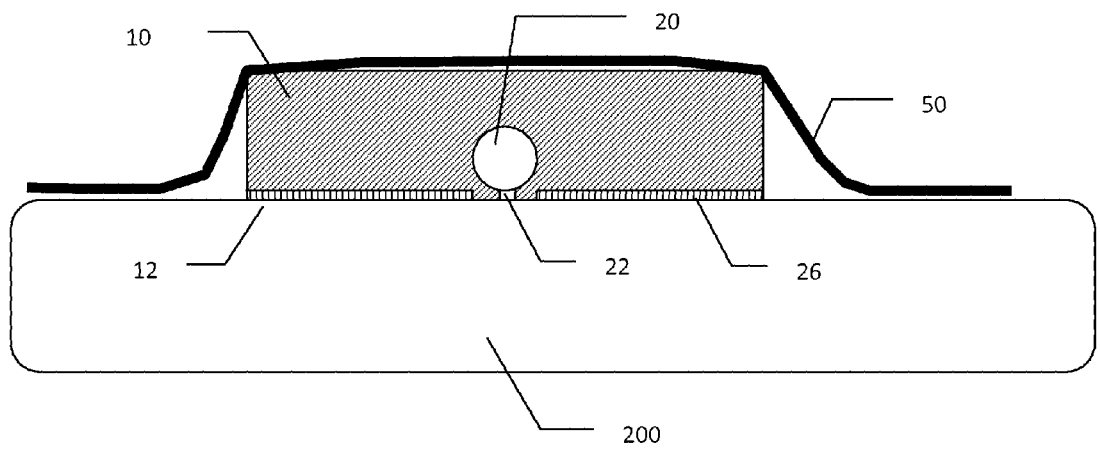
FIG. 8 illustrates an embodiment of the inventive percutaneous medical device dressing.

Referring now to FIG. 8, a cross-sectional view of dressing 10 installed on patient's skin 200 and attached to skin 200 by an optional adhesive layer 26 disposed on skin-facing lower surface 12 of dressing 10 and optionally within channel 20. Alternatively or in addition to optional adhesive layer 26, dressing 10 is removably attached to skin 200 by an overdressing 50 in the form of an adhesive tape or bandage applied over dressing 10. Overdressing 50 can be occlusive or semi-occlusive, such as adhesive tape, bandage, or polyurethane film.

Figure 9A:
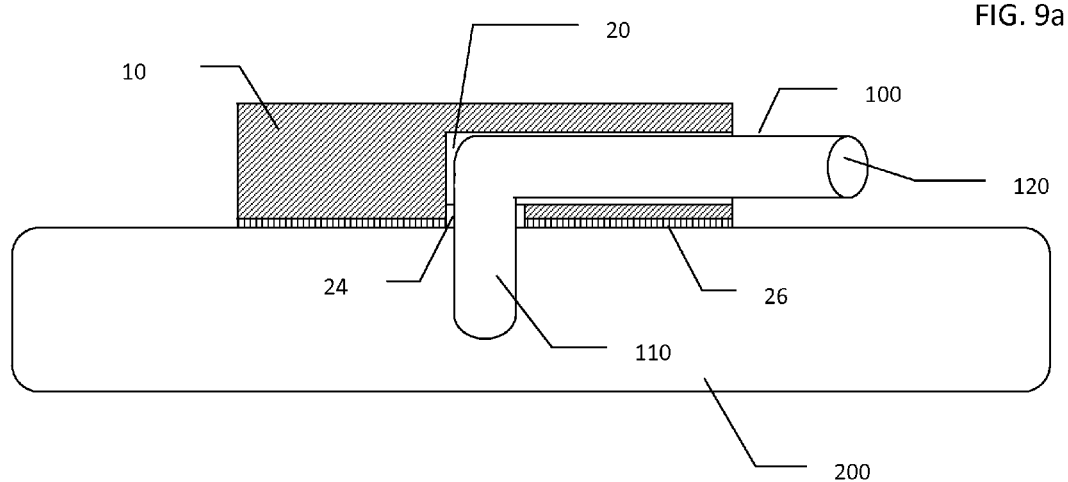
FIGS. 9a, 9b, 9c, 9d, 9e, 9f illustrate an embodiment of the inventive percutaneous medical device dressing.
Figure 9B:
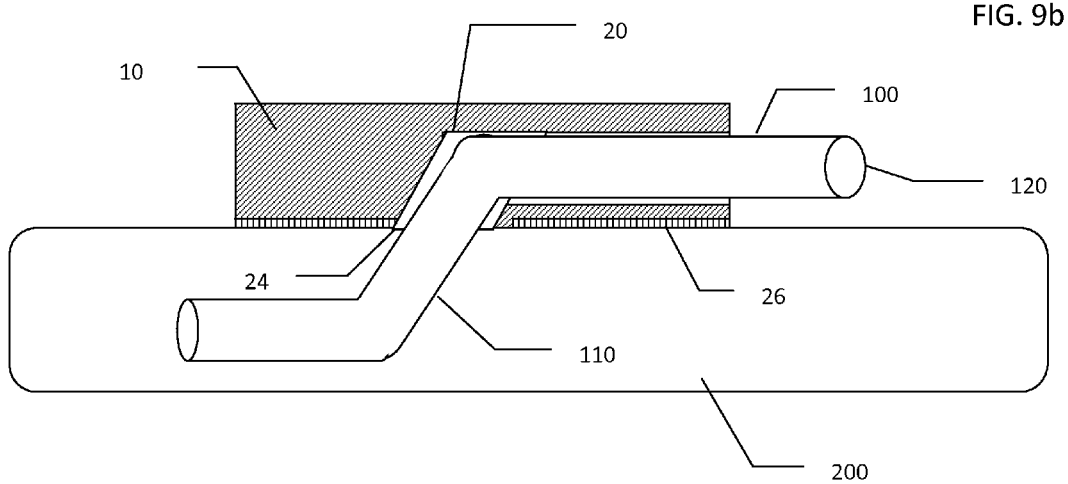

Referring now to FIGS. 9a and 9b, an alternative cross-sectional view is shown of dressing 10 that is installed on patient's skin 200 and removably attached to skin 200 by an optional adhesive layer 26 or overdressing 50 (not shown). Dressing 10 is applied around catheter or percutaneous medical device 100 so that the percutaneous medical device 100 is positioned in and held within channel 20.

Dressing 10 completely surrounds the wound or skin puncture site for the percutaneous medical device 100 thus preventing the ingress of contaminating or infectious matter and delivers anti-microbial active ingredient that is disposed within dressing 10.

At least the lower surface 12 of the dressing 10 and optionally all surfaces and optionally the body of dressing 10 are provided with an anti-microbial material in order to limit infection. Anti-microbial materials for use with medical dressing materials are well known in the art. The anti-microbial material may be impregnated in dressing 10 or provided as a thin film of an anti-microbial material on the surfaces of dressing 10, with at least skin-facing lower surface 12 having anti-microbial material. Optionally other surfaces, particularly surfaces of channel 20, circular opening 24, and gap 22 are also provided with the anti-microbial material. Optional adhesive layer 26 can also optionally contain anti-microbial material.

The material comprising drug eluting material of dressing 10 may be, for example, a porous sponge or hydrogel or solid polymeric matrix. Examples of materials include chitosan, polysaccharides, glycosaminoglycans, glycoproteins, proteins, silicones, PVA, alginates, oxidized regenerated cellulose, and other materials known to be capable of either reversibly binding to anti-microbial agents or serving as reservoirs for the diffusion of the anti-microbial agent.

While the positioning of percutaneous medical device 100 in FIG. 9a indicates that proximal end 110 piercing skin 200 is positioned under angle approximately perpendicular to the skin, the angle of percutaneous medical device 100 relative skin will vary depending on type of percutaneous medical device 100 and type of installation, from almost parallel to the skin at the point of entering the skin, to about 90 degrees or perpendicular to the skin. Typical angles can be from about 15 degrees to about 90 degrees as between percutaneous medical device 100 and the skin surface, such as 15, 30, 60, 80 degree angles. As it is further illustrated in FIG. 9b, the angle of percutaneous medical device 100 relative to the skin surface can be about 45 degrees.

Figure 9C:
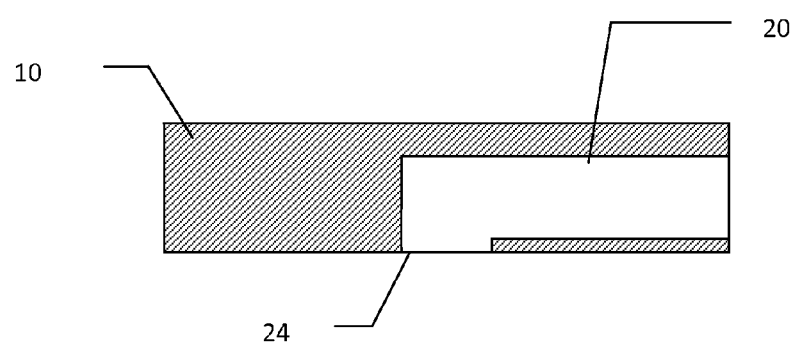
Figure 9D:
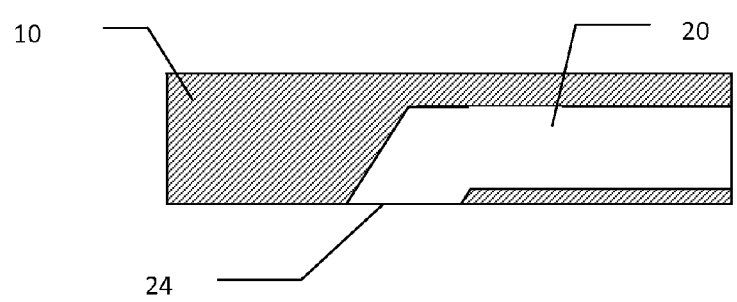

As further illustrated in cross-sectional views of dressing 10 presented in FIGS. 9c and 9d, channel 20 can optionally have perpendicular connection to circular opening 24, as shown in FIG. 9c, or optional an angular connection to circular opening 24, as shown in FIG. 9d. In the embodiments lacking optional circular opening 24, as shown in FIGS. 2a and 2b, percutaneous medical device 100 also can exit channel 20 at any angle from skin-facing lower surface 12.

Figure 9E:
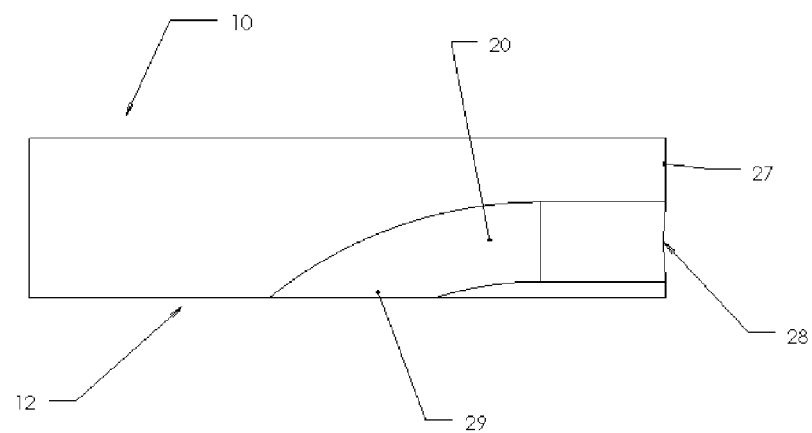
Figure 9F:
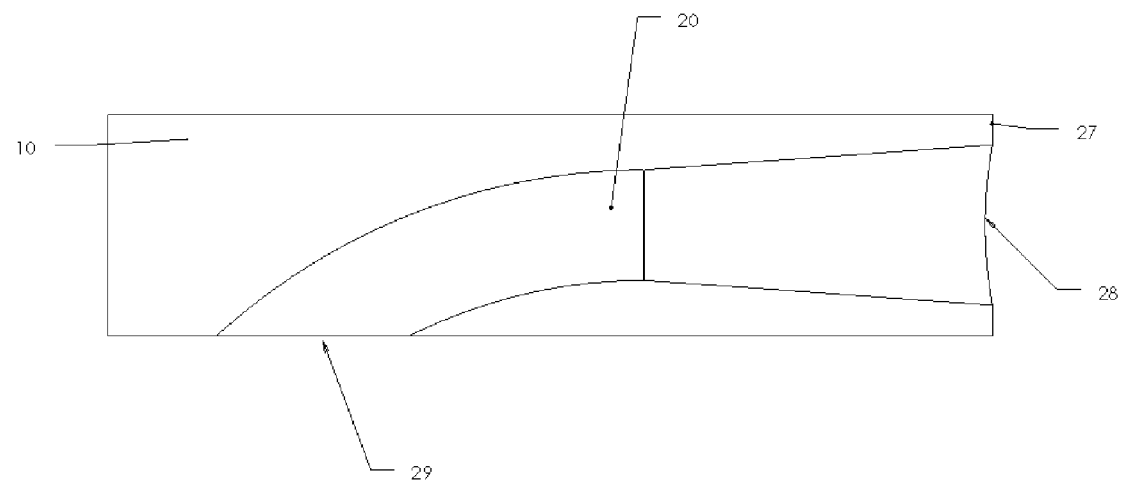

The embodiments shown in FIGS. 9e and 9f illustrate a cross-sectional view of dressing 10 with channel 20, whereas channel 20 has an entrance 28 within side wall 27 and an exit 29 within skin-facing lower surface 12 of dressing 10. Entrance 28 has substantially the same diameter as channel 20, and exit 29 has dimensions that are larger than the diameter of channel 20 enabling dressing 10 to accommodate flexible positioning of percutaneous medical device 100 (not shown) in channel 20, with percutaneous medical device 100 being shaped as needed for optimal ingress into the patient's body. The design of dressing 10 shown in FIGS. 9e and 9f facilitates a smooth bend of catheter or percutaneous medical device within channel 20, from being substantially parallel to the skin of the patient to an angle required to enter the skin of the patient.

An embodiment shown in FIG. 9f further illustrates a cross-sectional view of dressing 10 with channel 20, whereas channel 20 has within side wall 27 entrance 28 with a flared or conical shape having a diameter that is larger at entrance 28 relative to the diameter of channel 20. Flared or conical shape of entrance 28 facilitates positioning of dressing 10 in a coupled way with connectors or couplers or flanges positioned on catheter or percutaneous medical device 100 (not shown), whereby such connectors or couplers (not shown) installed on percutaneous medical device 100 (not shown) are inserted into flared or conically shaped entrance 28 and are fixedly positioned within entrance 28.

Figure 10:
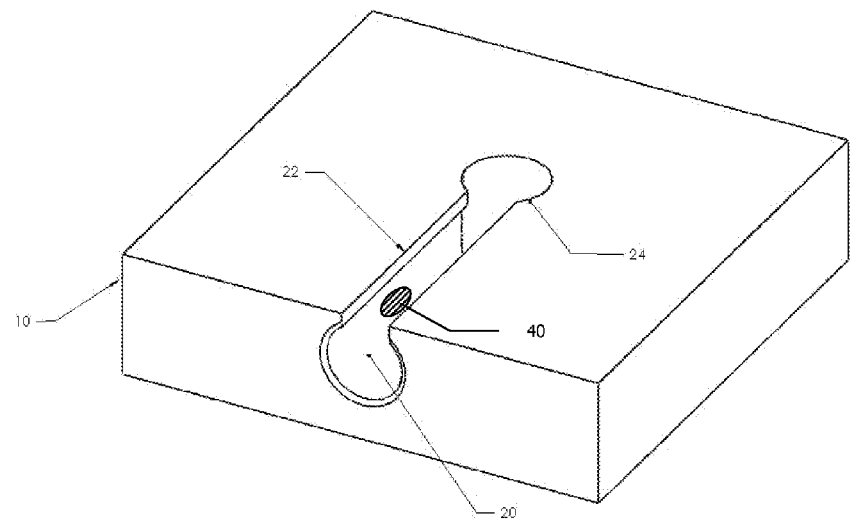
FIG. 10 illustrates an embodiment of the inventive percutaneous medical device dressing.

Referring now to FIG. 10, in one embodiment of the present invention, a small quantity of semi-solid viscous sealant or anti-microbial ointment 40 is disposed in channel 20 prior to applying dressing 10 over catheter or percutaneous medical device 100. In a preferred embodiment, sealant or anti-microbial ointment 40 is disposed in channel 20 during manufacturing of dressing 10.

Figure 11:
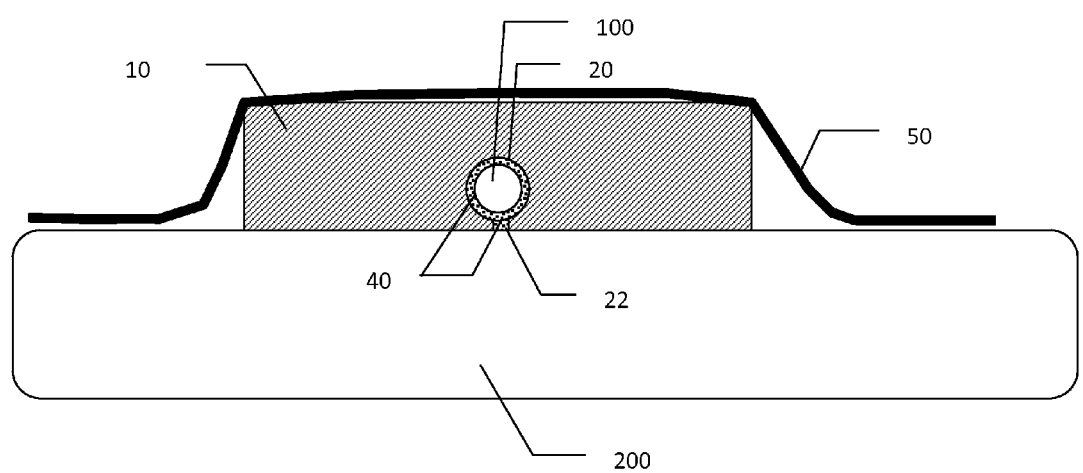
FIG. 11 illustrates an embodiment of the inventive percutaneous medical device dressing.

As illustrated in FIG. 11, upon positioning of catheter or percutaneous medical device 100 within channel 20, the semi-solid sealant or ointment 40 is displaced by the catheter along channel 20 walls and also into gap 22 and seals around catheter 100 and against skin 200. Semi-solid anti-microbial ointments and sealants are known in the art. Advantageously, sealing channel 20 with ointment 40 provides additional protecting against ingress of contaminating potentially infectious matter along channel 20.

Figure 12A:
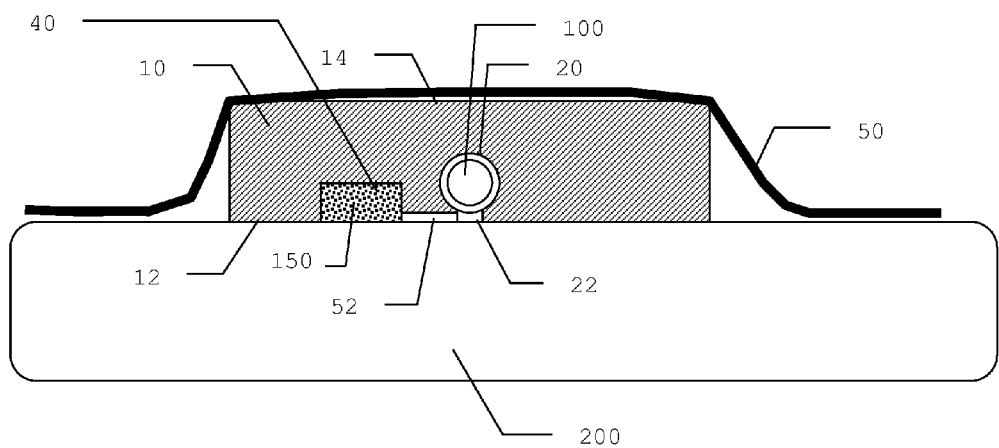
FIGS. 12a and 12b illustrate an embodiment of the inventive percutaneous medical device dressing.
Figure 12B:
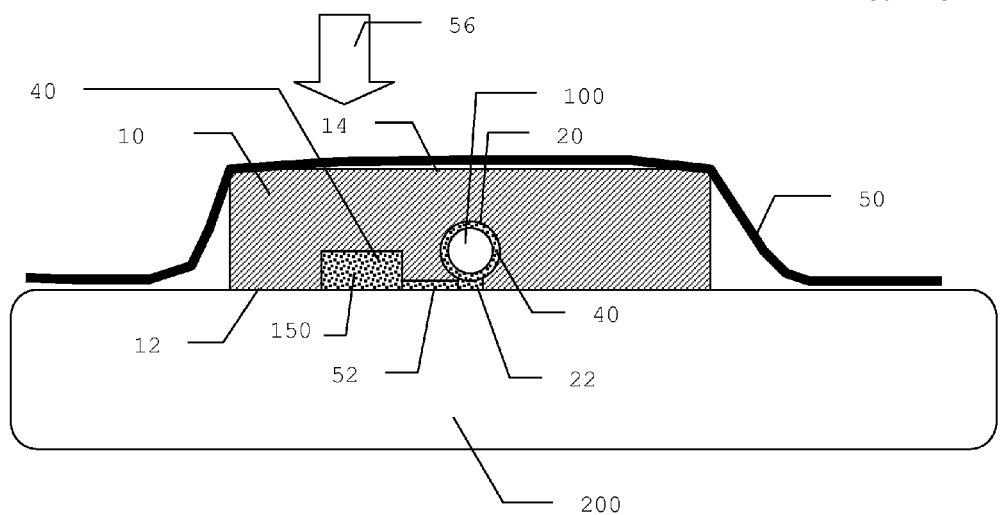

An embodiment of the present invention which is shown in FIG. 12a has a compartment 150 cut into lower surface 12 of dressing 10. Compartment 150 is filled with ointment 40 during manufacturing of dressing 10 and has a connecting channel 52 connecting compartment 150 to gap 22 or to channel 20 opening. After positioning of catheter or percutaneous medical device 100 within channel 20, the healthcare practitioner depresses upper surface 14 above compartment 150, with the approximate area of depressing being shown by arrow 56 above compartment 150, thus displacing ointment 40 through connecting channel 52 into channel 20 resulting in ointment 40 distributing between channel 20 walls and catheter 100 and into gap 22 and advantageously sealing around catheter 100 and against skin 200, as illustrated in FIG. 12b.

In the embodiments of the present invention shown in FIGS. 10, 11, and 12, the ointment or sealant 40 is optionally photo-crosslinkable. Photo-crosslinkable sealants and adhesives are known in the art. Actinic light (such as blue light or UV light) from a light source, such as a hand-held battery-operated or similar light source is then optionally used to cross-link the sealant after installation of dressing 10 over catheter 100 and after ointment or sealant 40 is displaced into channel 20. Cross-linked ointment or sealant 40 provides additional adhesive strength preventing displacement of dressing 10 against percutaneous medical device 100 and further preventing the ingress of the contamination along channel 20.

Figure 13A:
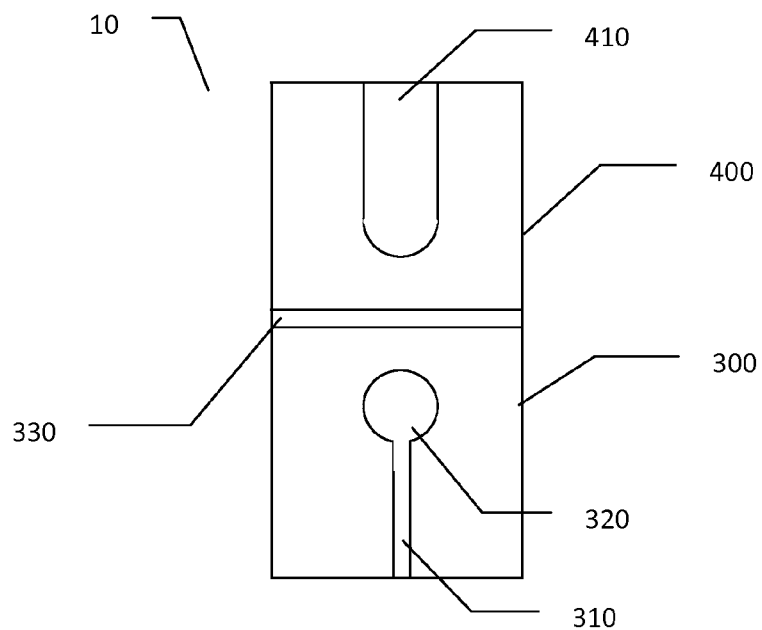
FIGS. 13a and 13b illustrate an embodiment of the inventive percutaneous medical device dressing.
Figure 13B:
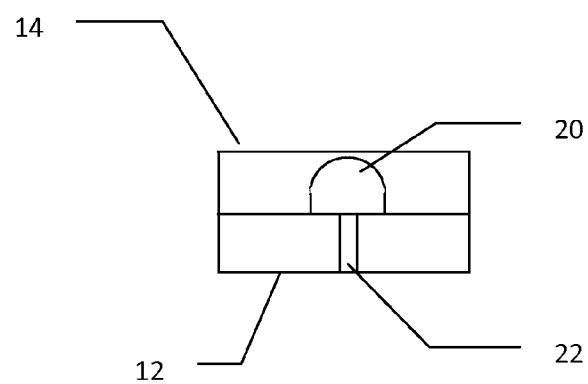

Referring now to FIGS. 13a and 13b, an embodiment of the present invention is shown, with FIG. 13a representing a top view and FIG. 13b representing a side view. As shown in FIGS. 13a and 13b, dressing 10 of a final shape substantially similar to the embodiments of FIGS. 1 through 12 is formed of two optionally linked subunits, lower portion 300 and upper portion 400. FIG. 13a illustrates a top view of dressing 10 prior to installation, dressing 10 comprising two foldably linked portions: lower portion 300 having circular cut 320 and slit 310 and upper portion 400 having a surface trench or channel 410. Lower portion 300 is foldably linked to upper portion 400 at the linking area 330. FIG. 13b shows an assembled dressing 10 with upper portion 400 folded at linking area 330 and positioned on top of lower portion 300, with percutaneous medical device or catheter 100 not shown. The resulting dressing 10 assembled of lower portion 300 and upper portion 400 is substantially similar to dressing 10 as shown in FIGS. 1 through 12.

Figure 14A:
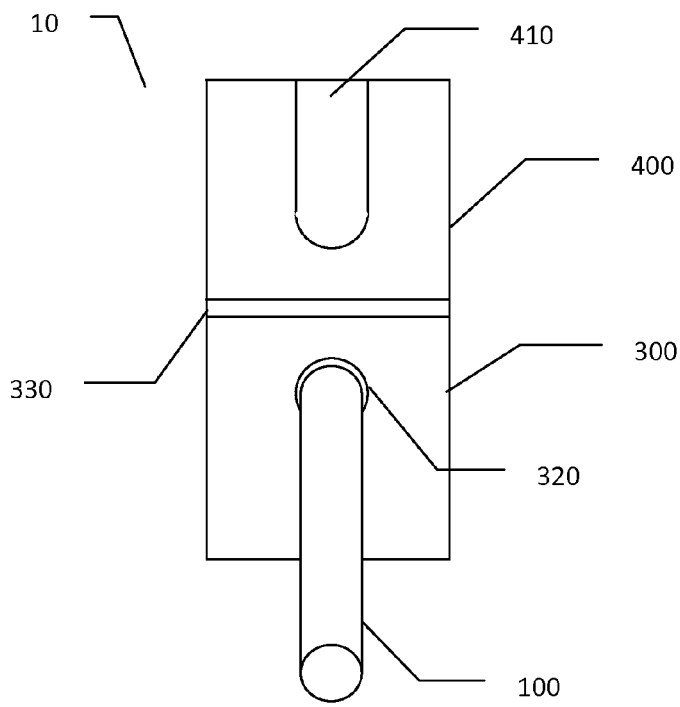
FIGS. 14a and 14b illustrate an embodiment of the inventive percutaneous medical device dressing.
Figure 14B:
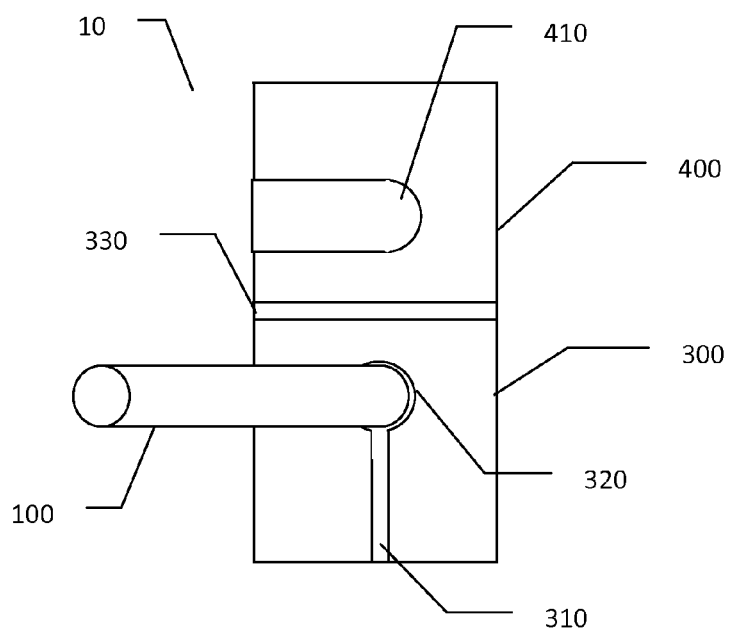

In use, as shown in FIGS. 14a and 14b, lower portion 300 is installed on percutaneous medical device or catheter 100 with the circular cut 320 surrounding the catheter and slit 310 going around and under the catheter 100. Percutaneous medical device or catheter 100 can be positioned aligned with slit 310 as shown in FIG. 14a or angular to slit 310, such as perpendicular to slit 310, as shown in FIG. 14b, with surface trench or channel 410 being also perpendicular to slit 310. Advantageously, angular positioning of percutaneous medical device or catheter 100 relative to slit 310 further improves the 360 degrees antimicrobial protective action of dressing 10.

After positioning lower portion 300 on percutaneous medical device or catheter 100 as shown in FIGS. 14a and 14b, upper portion 400 is folded at linking area 330 and positioned on top of lower portion 300 with surface channel 410 surrounding and covering percutaneous medical device or catheter 100. Optionally, an adhesive is disposed on at least one surface of lower portion 300 or upper portion 400 which are facing each other in assembled dressing 10, to assure structural integrity of assembled dressing 10. The resulting dressing 10 assembled of lower portion 300 and upper portion 400 is substantially similar to dressing 10 as shown in FIGS. 1 through 12. Advantageously, manufacturing of dressing 10 made of two subunits is simplified, whereby low cost web converting and high speed molding processes can be used to manufacture two-piece dressing 10.

Figure 15A:
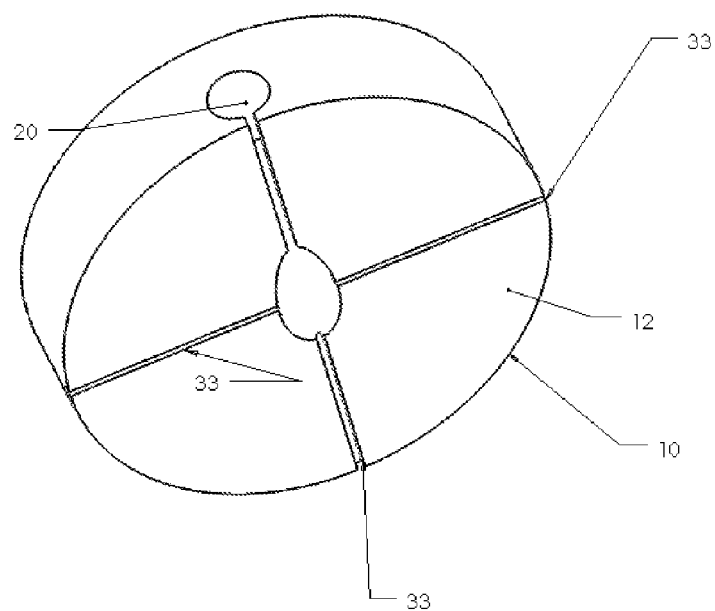
FIGS. 15a and 15b illustrate an embodiment of the inventive percutaneous medical device dressing.
Figure 15B:
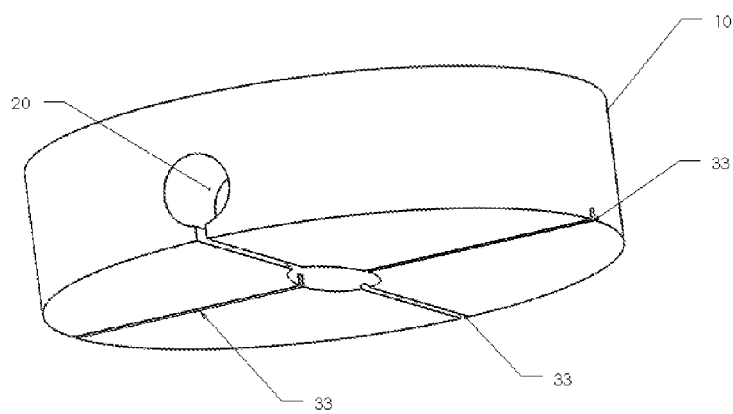

Referring now to FIGS. 15a and 15b, in certain embodiments of dressing 10 a plurality of grooves 33 are machined, molded, or cut into skin-facing lower surface 12 of dressing 10. Grooves 33 are adapted to facilitate the removal of fluids or other exudates from the area under the dressing. As shown in FIGS. 15a and 15b, grooves 33 are radially extending within lower surface 12 from approximately the center of dressing 10 to the periphery of dressing 10. The depth of grooves 33 is from about 0.1 mm to about 2 mm, such as 0.2 mm, 0.5 mm, or 1.0 mm. The width of grooves 33 is from about 0.1 mm to about 2 mm, such as 0.2 mm, 0.5 mm, 1.0 mm.

Figure 16A:
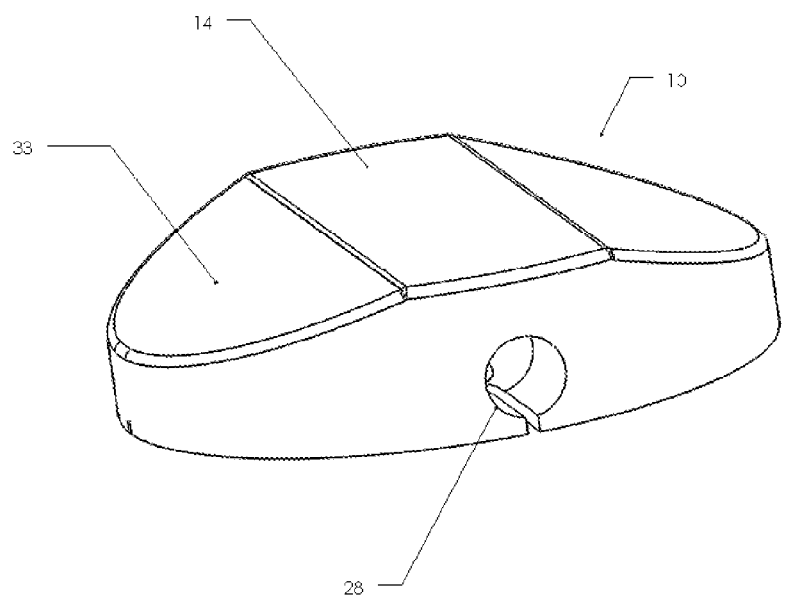
FIGS. 16a, 16b, 16c, and 16d illustrate an embodiment of the inventive percutaneous medical device dressing.
Figure 16B:
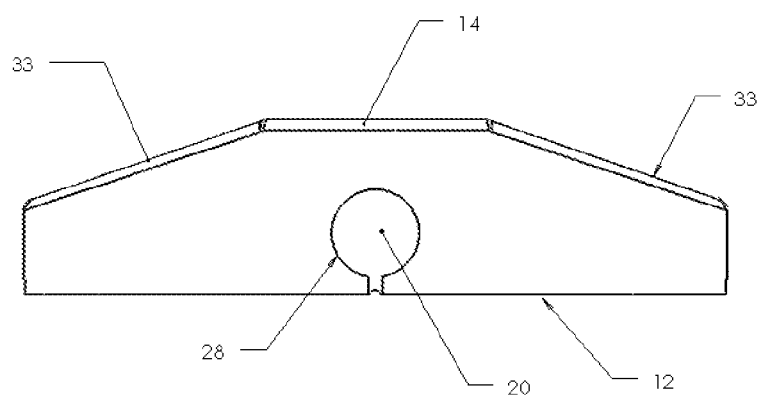
Figure 16C:
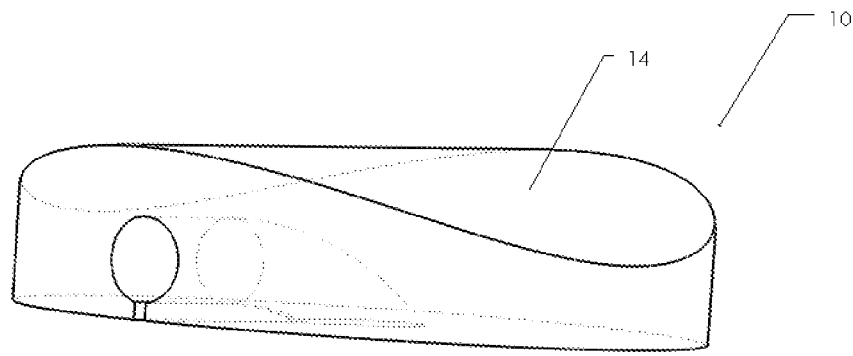
Figure 16D:
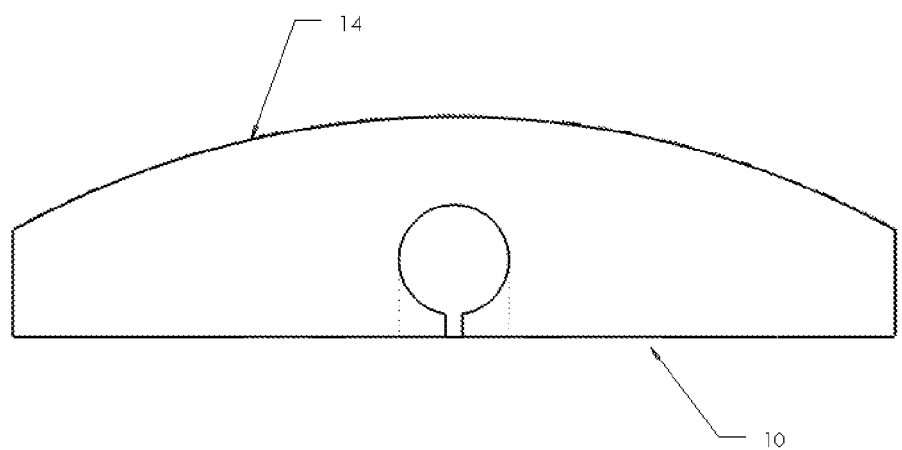

Referring now to FIGS. 16a, 16b, 16c, and 16d, in certain embodiments upper surface 14 of dressing 10 has the shape facilitating the application of overdressing 50 (not shown) in the form of adhesive tape or bandage applied over dressing 10. As shown in FIGS. 16a and 16b, flat surface areas 33 are cut into body of dressing 10 under angle, so that some horizontal, flat area remains on upper surface 14 adjoined by sloping down flat areas 33. As shown in FIGS. 16c and 16d, in one embodiment upper surface 14 is a continuous surface having a shape of a cylinder wall. Advantageously, embodiments shown in FIGS. 16a, 16b, 16c, and 16d facilitate uniform application of overdressing such as adhesive tape or bandage without tenting or gaps or air bubbles entrapped under overdressing or between overdressing and upper surface 14 of dressing 10.

Embodiments shown in FIGS. 16a, 16b, 16c, and 16d have a generally circular or elliptical shape of dressing 10. In other embodiments (not shown) dressing 10 has a rectangular or specifically square shape, further facilitating uniform application of overdressing over dressing 10.

Figure 17A:
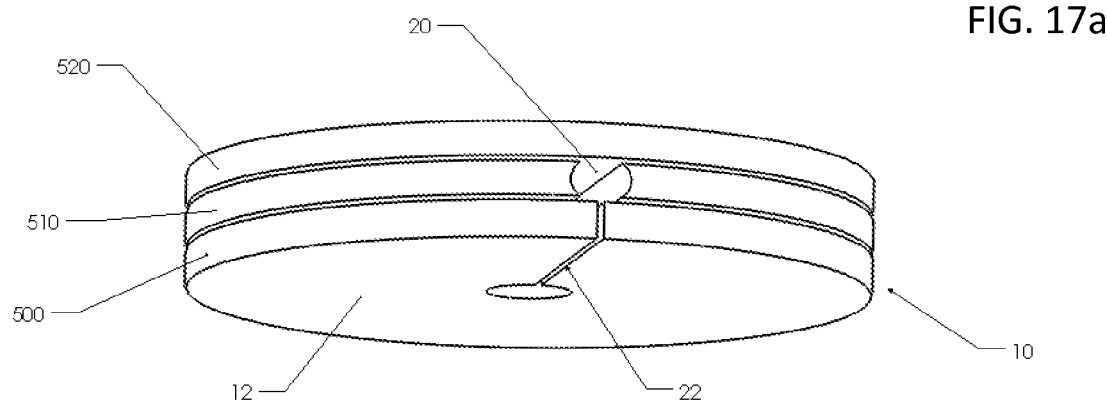
FIGS. 17a and 17b illustrate an embodiment of the inventive percutaneous medical device dressing.

Referring now to FIG. 17a, dressing 10 of final shape substantially similar to the embodiments of FIGS. 1 through 12 is formed of three optionally adhesively joined together subunits, lower disk 500, middle disk 510, and upper disk

Figure 17B:
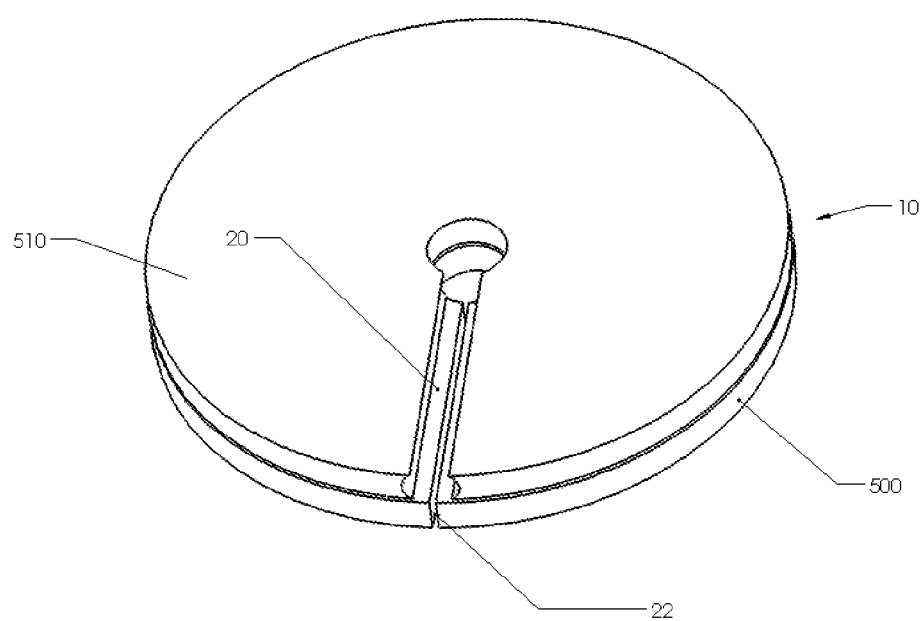

520. Lower disk 500 has slit or gap 22 cut radially from about the center of disk 500 to the periphery. Middle disk 510 has channel 20 cut radially from about the center of disk 510 to the periphery. Upper disk 520 forms covering layer of the assembly shown in FIG. 17*a*, with gap 22 aligned with channel 20. FIG. 17*b* illustrates the embodiment of FIG. 17*a* with upper disk 520 removed for better clarity, with gap 22 aligned with channel 20.

In one embodiment, all three disks 500, 510, and 520 are made of the same material, and are optionally joined together with an adhesive, preferably with gap 22 aligned with channel 22 as shown in FIGS. 17*a* and 17*b*. In an alternative embodiment, lower disk 500 has skin adhesive disposed on it; middle disk 510 is impregnated with anti-bacterial or anti-septic material; and upper disk 520 has water impermeable properties or water impermeable coating. Advantageously, manufacturing of dressing 10 made of three layers or three disks is simplified, whereby low cost web converting can be used to manufacture three-piece dressing 10.

Percutaneous medical devices for which the dressings above can be used include catheters, pins, implants and the like which pass through the skin and are indwelling for some considerable time. Exemplary of percutaneous medical devices are central venous catheters, peripheral venous catheters, Swan-Gaus pulmonary catheters, central nervous system implants (ex. external ventricular drainage and ventricular reservoirs), peritoneal dialysis catheters, such as for continuous ambulatory peritoneal dialysis and continuous cyclic peritoneal dialysis, hemodialysis catheters, transvenous pacemaker leads and temporary orthopedic pins. All of these percutaneous medical devices, when in place, have a portion of the device which is external, that is which is left protruding from the skin, and which can be the cause of infection.

In a preferred embodiment, dressing 10 is prepared by the steps of cross-linking a polymer which contains chemically reactive functionalities which react with a cross-linking reagent, where the cross-linking agent comprises greater that two reactive sites per molecule which are chemically reactive with functionalities on the biopolymer, to form a cross-linked polymer; optionally, forming the cross-linked biopolymer into a desired shape; then contacting the cross-linked polymer with a bioactive agent to reversibly bind the bioactive agent to the polymer to form the polymeric delivery vehicle. Preferably, the cross-linking reagent is a polyurethane or polyurethane urea having isocyanate side groups and/or end groups.

Examples of polymers which can be treated with a cross-linking agent according to the present invention include, but are not limited to proteins, peptides and polysaccharides. Preferred polymers are gelatin, collagen, and polysaccharides, particularly cellulose derivatives, as, for example, hydroxyethylcellulose. The thickness of the polymeric matrix may be varied as desired, depending upon the desired pharmaceutical dosage and duration of delivery. Ordinarily, a suitable matrix thickness will be in a range of about 0.1 to 1.0 centimeters.

The ratio of cross-linking agent to polymer will depend in part on the particular polymer and the bioactive agent with which it is intended to be used. It will be understood that mixtures of different polymers may also be utilized. However, generally, it will be useful to employ a weight ratio of cross-linking agent to biopolymer of from about 20:1 to about 1:1. It will be realized that suitable polymerization initiators may be utilized to initiate the polymerization reaction, which include, but are not limited to azobisisobutylnitrile, peroxide initiators, such as benzoyl peroxide, isopropyl peroxide, and the like. Although polyurethane and polyurethane ureas are the preferred cross-linking agents, other cross-linking agents may be suitable, such as alkylene polyacrylates, alkylene polymethacrylates, alkylene glycolpolymethacrylates, polyalkylene glycolpolymethacrylates, polyaldehydes as well as other cross-linking agents which will cross-link molecules with reactive protic groups. A preferred cross-linking agent is a polyether polyisocyanate that has greater than 2 free isocyanate groups/molecule.

The top and bottom dressing materials can be formed by molding or casting before cross-linking or, after cross-linking, by cutting. The cross-linked polymer will then be loaded with the desired bioactive agent(s). Typically, the bioactive agent is dissolved in a suitable solvent and then placed in fluid contact with the cross-linked polymer by immersion. The loading of the biopolymer may be readily determined based upon the uptake of the biopolymer of the bioactive agent.

In a preferred method for forming the loaded cross-linked polymer, the bioactive agent is dissolved in water at a suitable concentration, typically about 1-2% by weight, and the cross-linked biological polymer is immersed therein for a period of about 240 minutes. At ambient temperature (about 20-25° C.), the polymer is then extracted from the solvent, allowed to air dry or is lyophilized, and is then ready for use.

Alternatively, the cross-linked polymer may be loaded with the bioactive agent, then dried, then cut to a suitable form for use.

In another preferred method, the bioactive agent and biopolymer are dissolved in an aqueous solvent before cross-linking and the bioactive agent is bound to the polymer. Typical agent: biopolymer weight ratios are in the range of about 1:100 to 5:100 in solution. The polymer is then cross-linked by treatment with the cross-linking agent.

The invention being thus described, it will be apparent that the same may be varied in many ways. Such variations are not to be regarded as a departure from the spirit and scope of the invention, and all such modifications as would be obvious to one skilled in the art are intended to be included within the scope of the following claims.

We claim:

1. A percutaneous device dressing for use with a percutaneous medical device that has punctured the skin of a patient and which has a portion of the percutaneous medical device protruding from the skin, comprising:
   a) a dressing body formed from a flexible material and having upper and lower surfaces and an exterior side wall, with the lower surface being skin facing in use,
   b) a channel formed in a region between the lower and upper surfaces of the dressing body and extending to the exterior side wall, the channel adapted to accept the percutaneous medical device protruding from the skin, wherein the channel has a shape that surrounds at least a portion of the percutaneous medical device protruding from the skin;
   c) a bioactive agent that is incorporated into the dressing body and/or onto the lower surface of the dressing body, and
   d) a gap within the lower surface, the gap providing an opening of the channel to the lower surface,
   wherein the gap is adapted to allow positioning of the dressing over the percutaneous medical device,
   wherein the gap is adapted to allow the percutaneous medical device to be at least partially disposed within the channel,
   wherein said channel is machined, cut, or molded within said dressing body, wherein said gap is aligned with said channel and runs along the entire length of said channel, and wherein said gap is positioned in the lower surface and radiates from a substantially central point of the dressing body to the exterior side wall, and wherein said gap is positioned symmetrically in the center of said channel.

2. A dressing according to claim 1 wherein the bioactive agent is an antimicrobial agent.

3. A dressing according to claim 2 wherein said antimicrobial agent comprises chlorhexidine.

4. A dressing according to claim 3, wherein the dressing is secured to the skin of a patient by an adhesive disposed on the lower surface, by an overdressing layer, or combinations thereof.

5. A dressing according to claim 3, wherein the channel has an entrance on the exterior side wall of the dressing body and an exit on the lower surface of the dressing body.

6. A dressing according to claim 5, wherein the gap has a width equal to or less than the width of the channel.

7. A dressing according to claim 6, wherein the entrance of the channel is flared, and wherein the entrance is adapted to accommodate coupling or connectors with the percutaneous medical device.

8. A dressing according to claim 1, further comprising a semi-solid material disposed within the channel,
wherein the semi-solid material is a sealant, an anti-microbial ointment, or combination thereof, and
wherein the semi-solid material is optionally photo cross-linkable.

9. A dressing according to claim 8, further comprising a compartment formed within the lower surface,
wherein the compartment is in fluid communication with the channel,
wherein the compartment is filled with the semi-solid material.

10. A dressing according to claim 1, wherein the dressing has a plurality of grooves in the lower surface.

11. A dressing according to claim 1, wherein the dressing body has an upper portion and a lower portion, the upper portion and the lower portion being foldably linked,
wherein for application and use, the upper portion is folded onto the lower portion,
wherein the lower portion comprises the gap and the upper portion comprises the channel.

12. A dressing according to claim 1, wherein the dressing body comprises a lower subunit, a middle subunit, and an upper subunit,
wherein the lower subunit forms the lower surface and has the gap that radiates from a substantially central point on the lower subunit to the exterior sidewall,
wherein the middle subunit has the channel that radiates from a substantially central point on the middle subunit,
wherein the upper subunit forms the upper surface,
wherein the gap and the channel are aligned, and
wherein the lower subunit, the middle subunit, and the upper subunit are optionally adhesively joined together.

13. A method of dressing the puncture she of a percutaneous medical device that has punctured the skin of a patient and which has a portion of the percutaneous medical device protruding from the skin, comprising the steps of a) providing a dressing body formed from a flexible material and having upper and lower surfaces, an exterior side wall, and a channel formed in a region between the lower and upper surfaces of the dressing body and extending to the exterior side wall, said dressing body having a gap within the lower surface, the gap providing an opening of the channel to the lower surface, wherein said channel is machined, cut, or molded within said dressing body, wherein said gap is aligned with said channel and which runs along the entire length of said channel, wherein said gap is positioned symmetrically in the center of said channel, wherein said gap is positioned in the lower surface and radiates from a substantially central point of the dressing body to the exterior side wall, and wherein the gap is adapted to allow positioning of the dressing over the percutaneous medical device and adapted to allow the percutaneous medical device to be at least partially disposed within the channel, b) positioning the dressing body over the puncture site with the lower surface facing the skin, and c) sliding the percutaneous medical device into the channel, allowing the channel to accept at least a portion of the percutaneous medical device protruding from the skin to cover a perimeter region around the puncture site proximate to percutaneous medical device protruding from the skin with the dressing body.

14. A method according to claim 13, wherein dressing body further comprises a bioactive agent that is an antimicrobial agent.

15. A method according to claim 14, wherein said antimicrobial agent comprises chlorhexidine.

16. A method according to claim 15, further comprising the step of securing the dressing body to the skin of a patient by an adhesive disposed on the lower surface, by an overdressing layer, or combinations thereof.

17. A method according to claim 16, wherein the overdressing layer is an adhesive film.

18. A method according to claim 16 wherein the dressing body further comprises a compartment that is in fluid communication with the channel and contains a semi-solid material, further comprising the step of pressing on the upper surface of the dressing body and releasing the semi-solid material from the compartment into the channel after the step of covering a perimeter around the puncture site proximate to percutaneous medical device protruding from the skin with the dressing body, wherein the semi-solid material is a sealant, an anti-microbial ointment, or combination thereof.

19. A method according to claim 13, further comprising the step of disposing a semi-solid material within the channel, wherein the semi-solid material is a sealant, an anti-microbial ointment, or combination thereof.

\* \* \* \* \*